United States Patent [19]

Mohr et al.

[11] Patent Number: 5,994,603

[45] Date of Patent: Nov. 30, 1999

[54] METHYLATION OF TOLUENE TO PARA-XYLENE

[75] Inventors: Gary D. Mohr, League City; Robert Scott Smith, Houston, both of Tex.

[73] Assignee: Exxon Chemical Patents Inc., Houston, Tex.

[21] Appl. No.: 08/865,634

[22] Filed: May 29, 1997

Related U.S. Application Data

[60] Provisional application No. 60/018,583, May 29, 1996, provisional application No. 60/018,550, May 29, 1996, provisional application No. 60/018,547, May 29, 1996, provisional application No. 60/018,390, May 29, 1996, provisional application No. 60/018,546, May 29, 1996, and provisional application No. 60/018,551, May 29, 1996.

[51] Int. Cl.$^6$ .............................. C07C 2/68; C07C 1/00; B01J 29/06

[52] U.S. Cl. ........................... 585/467; 585/454; 502/67

[58] Field of Search .................................. 585/467, 454; 502/67

[56] References Cited

U.S. PATENT DOCUMENTS

| | | | |
|---|---|---|---|
| 3,965,207 | 6/1976 | Weinstein | 260/671 M |
| 4,002,697 | 1/1977 | Chen | 260/671 M |
| 4,100,215 | 7/1978 | Chen | 260/671 M |
| 4,289,607 | 9/1981 | Kokotailo | 208/120 |
| 4,358,362 | 11/1982 | Smith et al. | 208/91 |
| 4,358,395 | 11/1982 | Haag et al. | 252/441 R |
| 4,449,890 | 4/1984 | Herkes | 585/467 |
| 4,670,616 | 6/1987 | De Simone et al. | 585/467 |
| 4,847,224 | 7/1989 | Fajula et al. | 502/67 |
| 5,349,113 | 9/1994 | Chang et al. | 585/475 |

FOREIGN PATENT DOCUMENTS

| | | | |
|---|---|---|---|
| WO9212928 | 8/1992 | WIPO | C01B 33/34 |
| WO96/16004 | 5/1996 | WIPO | C07C 2/66 |
| WO9814415 | 4/1998 | WIPO | C07C 1/20 |

OTHER PUBLICATIONS

"MFI"; internet search document; pp. 1–3, Jun. 1998.

"MEL"; internet serach document; pp. 1–3, Jun. 1998.

*Primary Examiner*—Walter D. Griffin
*Assistant Examiner*—Thuan D. Dang
*Attorney, Agent, or Firm*—Edward F. Sherer

[57] ABSTRACT

A process is provided for the production of paraxylene by the methylation of toluene in the presence of a zeolite bound zeolite catalyst. The catalyst comprises first zeolite crystals which are bound together by second zeolite crystals. When used to methylate toluene to para-xylene, the zeolite bound zeolite catalyst has a para-xylene selectivity greater than thermodynamic equilibrium. This selectivity can be enhanced by selectivating the catalyst.

26 Claims, No Drawings

5,994,603

METHYLATION OF TOLUENE TO PARA-XYLENE

This is a provisional application of Ser. Nos. 60/018,583, 60/018,550, 60/018,547, 60/018,390, 60/018,546 and 60/018,551 all filed on May 29, 1996.

FIELD OF THE INVENTION

This invention relates to a process for the production of xylenes by catalytic methylation of toluene in the presence of a zeolite bound zeolite catalyst. In addition, this invention relates a process for the selective production of xylene by catalytic methylation of toluene in the presence of a selectivated zeolite bound zeolite catalyst.

BACKGROUND OF THE INVENTION

Of the xylene isomers, i.e., ortho-, meta- and para-xylene, the paraxylene is of particular value as a chemical intermediate in a number of applications being useful in the manufacture of terephthalic acid which is an intermediate in the manufacturer of synthetic fibers. One process for manufacturing para-xylene is by disproportionation of toluene into xylenes. One of the disadvantages of this process is that large quantities of benzene are also produced. Another process used to obtain para-xylene involves the isomerization of a feedstream that contains non-equilibrium quantities of mixed ortho- and meta-xylene isomers and is lean with respect to para-xylene content. A disadvantage of this process is that the separation of the para-xylene from the other isomers is expensive.

Zeolites are comprised of a lattice of silica and optionally alumina combined with exchangeable cations such as alkali or alkaline earth metal ions. Although the term "zeolites" includes materials containing silica and optionally alumina, it is recognized that the silica and alumina portions may be replaced in whole or in part with other oxides. For example, germanium oxide, tin oxide, phosphorous oxide, and mixtures thereof can replace the silica portion. Boron oxide, iron oxide, gallium oxide, indium oxide, and mixtures thereof can replace the alumina portion. Accordingly, the terms "zeolite", "zeolites" and "zeolite material", as used herein, shall mean not only materials containing silicon and, optionally, aluminum atoms in the crystalline lattice structure thereof, but also materials which contain suitable replacement atoms for such silicon and aluminum, such as gallosilicates, silicoaluminophosphates (SAPO) and aluminophosphates (ALPO). The term "aluminosilicate zeolite", as used herein, shall mean zeolite materials consisting essentially of silicon and aluminum atoms in the crystalline lattice structure thereof.

Processes have been proposed for the production of xylenes by the methylation of toluene using a zeolite catalyst. For instance, U.S. Pat. No. 3,965,207 involves the methylation of toluene using a zeolite catalyst such as a ZSM-5. U.S. Pat. No. 4,670,616 involves the production of xylenes by the methylation of toluene using a borosilicate molecular sieve which is bound by a binder such as alumina, silica, or alumina-silica.

Synthetic zeolites are normally prepared by the crystallization of zeolites from a supersaturated synthesis mixture. The resulting crystalline product is then dried and calcined to produce a zeolite powder. Although the zeolite powder has good adsorptive properties, its practical applications are severely limited because it is difficult to operate fixed beds with zeolite powder. Therefore, prior to using in commercial processes, the zeohte crystals are usually bound.

The zeolite is typically bound by forming a zeolite aggregate such as a pill, sphere, or extrudate. The extrudate is usually formed by extruding the zeolite in the presence of a non-zeolitic binder and drying and calcining the resulting extrudate. The binder materials used are resistant to the temperatures and other conditions, e.g., mechanical attrition, which occur in various hydrocarbon conversion processes. Examples of binder materials include amorphous materials such as alumina, silica, titania, and various types of clays. It is generally necessary that the zeolite be resistant to mechanical attrition, that is, the formation of fines which are small particles, e.g., particles having a size of less than 20 microns.

Although such bound zeolite aggregates have much better mechanical strength than the zeolite powder, when such a bound zeolite is used for toluene methylation, the performance of the catalyst, e.g., activity, selectivity, activity maintenance, or combinations thereof, can be reduced because of the binder. For instance, since the amorphorous binder is typically present in an amount of up to about 50 wt. % of zeolite, the binder dilutes the adsorptive properties of the zeolite aggregate. In addition, since the bound zeolite is prepared by extruding or otherwise forming the zeolite with the binder and subsequently drying and calcining the extrudate, the amorphous binder can penetrate the pores of the zeolite or otherwise block access to the pores of the zeolite, or slow the rate of mass transfer to the pores of the zeolite which can reduce the effectiveness of the zeolite when used in hydrocarbon conversion processes. Furthermore, when such a bound zeolite is used in catalytic conversions processes such as toluene methylation, the binder may affect the chemical reactions that are taking place within the zeolite and also may itself catalyze undesirable reactions which can result in the formation of undesirable products.

SUMMARY OF THE INVENTION

The present invention is directed to a process for producing paraxylene by the reaction of toluene and a methylation agent under conversion conditions utilizing a zeolite bound zeolite catalyst which comprises first crystals of a first intermediate pore size zeolite and a binder comprising second crystals of a second zeolite.

In another embodiment, there is provided a process for selectively producing para-xylene in preference to meta- or ortho-xylene by the reaction of toluene and a methylation agent under conversion conditions in the presence of the zeolite bound zeolite catalyst which has been selectivated by depositing a selectivation agent thereon.

Compared to a conventional thermodynamic equilibrium xylene mixture in which the para:meta:ortho ratio is approximately 1:2:1, the process can achieve a xylene product in which the para-xylene content may exceed 70 percent. The improved yields of para-xylene reduces the cost of separation of para-xylene from other xylene isomers.

DETAILED DESCRIPTION OF THE INVENTION

The zeolite bound zeolite catalyst used in the process of the present invention comprises first crystals of an acidic intermediate pore size first zeolite and a binder comprising second crystals of a second zeolite. The use of second zeolite crystals as a binder results in a catalyst which provides a means for controlling undesirable reactions taking place on or near the surface of the first zeolite crystals and can have improved mass transfer of reactants and greater access to and from the pores of the zeolite.

Unlike zeolite catalysts bound with amorphous material such as silica or alumina to enhance the mechanical strength of the zeolite, the zeolite bound zeolite catalyst used in the process of the present invention does not contain significant amounts of non zeolitic binders. Preferably, the zeolite bound zeolite catalyst contains less than 10 percent by weight based on the total weight of the first and second zeolite of non-zeolitic binder, more preferably contains less than 5 percent by weight, and, most preferably, the first and second zeolite are substantially free of non-zeolitic binder. Preferably, the second zeolite crystals bind the first zeolite crystals by adhering to the surface of the first zeolite crystals thereby forming a matrix or bridge structure which also holds the first crystals particles together. More preferably, the second zeolite crystals bind the first zeolite by intergrowing so as to form a coating or partial coating on the larger first zeolite crystals and, most preferably, the second zeolite crystals bind the first zeolite crystals by intergrowing to form an attrition resistant over-growth over the first zeolite crystals.

Although the invention is not intended to be limited to any theory of operation, it is believed that one of the advantages of the zeolite bound zeolite catalyst when used in the process of the present invention is obtained by the second zeolite crystals controlling the accessibility of the acid sites on the external surfaces of the first zeolite to reactants. Since the acid sites existing on the external surface of a zeolite catalyst are not shape selective, these acid sites can adversely affect reactants entering the pores of the zeolite and products exiting the pores of the zeolite. In line with this belief, since the acidity of the second zeolite can be carefully selected, the second zeolite does not significantly adversely affect the reactants exiting the pores of the first zeolite which can occur with conventionally bound zeolite catalysts and may beneficially affect the aromatic selectivity of a dehydrogenation process and also the reactants exiting the pores of the first zeolite. Still further, since the second zeolite is not amorphous but, instead, is a molecular sieve, hydrocarbons have increased access to the pores of the first zeolite during the aromatization process.

The terms "acidity", "lower acidity" and "high acidity" as applied to zeolite are know to persons skilled in the art. The acidic properties of zeolite are well known. However, with respect to the present invention, a distinction must be made between acid strength and acid site density. Acid sites of a zeolite can be a Bronstead acid or a Lewis acid. The density of the acid sites and the number of acid sites are important in determining the acidity of the zeolite. Factors directly influencing the acid strength are (i) the chemical composition of the zeolite framework, i.e., relative concentration and type of tetrahedral atoms, (ii) the concentration of the extra-framework cations and the resulting extra-framework species, (iii) the local structure of the zeolite, e.g., the pore size and the location, within the crystal or at/near the surface of the zeolite, and (iv) the pretreatment conditions and presence of co-adsorbed molecules. The amount of acidity is related to the degree of isomorphous substitution provided, however, such acidity is limited to the loss of acid sites for a pure $SiO_2$ composition. As used herein, the terms "acidity", "lower acidity" and "higher acidity" refers to the concentration of acid sites irregardless of the strength of such acid sites which can be measured by ammonia adsorption.

The first zeolite used in the zeolite bound zeolite catalyst is an intermediate pore size zeolite. Intermediate pore size zeolites have a pore size from about 5 to about 7 Å and include, for example, AEL, MFI, MEL, MFS, MEI, MTW, EUO, MTT, HEU, FER, and TON structure type zeolites. These zeolites are described in "Atlas of Zeolite Structure Types", eds. W. H. Meier and D. H. Olson, Butterworth-Heineman, Third Edition, 1992, which is hereby incorporated by reference. Examples of specific intermediate pore size zeolites include ZSM-5, ZSM-11, ZSM-12, ZSM-22, ZSM-23, ZSM-34, ZSM-35, ZSM-38, ZSM-48, ZSM-50, and ZSM-57. Preferred first zeolites are galliumsilicate zeolites having an MFI structure and aluminosilicate zeolites having an MFI structure.

The term "average particle size" as used herein, means the average diameter of the crystals, e.g., number average of the major axis and minor axis.

The average crystal size of the crystals of the first zeolite is preferably from about 0.1 micron to about 15 microns, more preferably from about 1 to about 6 microns.

Procedures to determine crystal size are know to persons skilled in the art. For instance, crystal size may be determined directly by taking a suitable scanning electron microscope (SEM) picture of a representative sample of the crystals.

Intermediate pore size first zeolites will generally comprise a composition having the following molar relationship:

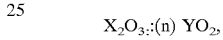

$$X_2O_3:(n)\ YO_2,$$

wherein X is a trivalent element such as aluminum and gallium and Y is a tetravalent element such as silicon, tin, and/or germanium; and n has a value greater than 12, said value being dependent upon the particular type of zeolite. When the intermediate pore size zeolite is a MFI structure type zeolite, n is preferably greater than 20.

As known to persons skilled in the art, the acidity of a zeolite can be reduced using many techniques such as by steaming. In addition, the acidity of a zeolite is dependent upon the form of the zeolite with the hydrogen form having the highest acidity and other forms of the zeolite such as the sodium form having less acidity than the acid form. Accordingly, the mole ratios of silica to alumina and silica to gallia disclosed herein shall include not only zeolites having the disclosed mole ratios, but shall also include zeolites not having the disclosed mole ratios but having equivalent catalytic activity.

When the first zeolite is an aluminosilicate zeolite, the first zeolite will preferably have a silica to alumina mole ratio from 10:1 to 300:1.

When the first zeolite is a gallium silicate zeolite, the zeolite preferably comprises a composition having the following molar relationship:

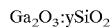

$$Ga_2O_3:ySiO_2$$

wherein y is between about 10 and about 150. The zeolite framework may contain only gallium and silicon atoms or may also contain a combination of gallium, aluminum, and silicon. When the first zeolite is a MFI structure type gallium silicate zeolite, the second zeolite will preferably be an intermediate pore size zeolite having a silica to gallia mole ratio greater than 100. The second zeolite can also have higher silica to gallia mole ratios, e.g., greater than 200, 500, 1000, etc.

The second zeolite will usually have an intermediate pore size and have less acid activity then the first zeolite. Preferably, the second zeolite will be substantially non-acidic and will have the same structure type as the first zeolite. The preferred second zeolites are aluminosilicate zeolites having a silica to alumina mole ratio greater than 100 such as low acidity ZSM-5. If the second zeolite is an aluminosilicate zeolite, the second zeolite will generally have a silica to alumina mole ratio greater than 200:1, e.g., 500:1; 1,000:1, etc., and in some applications will contain no more than trace amounts of alumina. The second zeolite can also be silicalite, i.e., a MFI type substantially free of alumina, or silicalite 2, a MEL type substantially free of alumina. The second zeolite is usually present in the zeolite bound zeolite catalyst in an amount in the range of from about 10% to 60% by weight based on the weight of the first zeolite and, more preferably, from about 20% to about 50% by weight.

The second zeolite crystals preferably have a smaller size than the first zeolite crystals and more preferably will have an average particle size of less than 1 micron, and most preferably will have an average particle size from about 0.1 to about 0.5 micron. The second zeolite crystals, in addition to binding the first zeolite particles and maximizing the performance of the catalyst will preferably intergrow and form an over-growth which coats or partially coats the first zeolite crystals. Preferably, the crystals will be resistant to attrition.

The zeolite bound zeolite catalyst used in the process of the present invention is preferably prepared by a three step procedure. The first step involves the synthesis of the first zeolite crystals prior to converting it to the zeolite bound zeolite catalyst. Processes for preparing the first zeolite are known in the art. For example, with respect to the preparation of a MFI type aluminosilicate zeolite, a preferred process comprises preparing a solution containing tetrapropyl ammonium hydroxide or bromide, alkali metal oxide, an oxide of aluminum, an oxide of silicon and water, and then heating the reaction mixture to a temperature of 80° C. to 200° C. for a period of from about four hours to eight days. The resulting gel forms solid crystal particles which are separated from the reaction medium, washed with water and dried. The resulting product may then be optionally calcined in air at temperatures of 400–550° C. for a period of 10–40 hours to remove tetrapropylammonium (TPA) cations.

Next, a silica-bound aluminosilicate zeolite can be prepared preferably by mixing a mixture comprising the aluminosilicate zeolite crystals, a silica gel or sol, water and optionally an extrusion aid and, optionally, the metal component until a homogeneous composition in the form of an extrudable paste develops. The silica binder used in preparing the silica bound zeolite aggregate is preferably a silica sol and preferably contains only very minor amounts of alumina or gallium, e.g., less than 2,000 ppm. The amount of silica used is such that the content of the zeolite in the dried extrudate will range from about 40 to 90% by weight, more preferably from about 50 to 80% by weight, with the balance being primarily silica, e.g. about 20 to 50% by weight silica.

The resulting paste can be molded, e.g. extruded, and cut into small strands, e.g., approximately 2 mm diameter extrudates, which can be dried at 100–150° C. for a period of 4–12 hours and then calcined in air at a temperature of from about 400° C. to 550° C. for a period of from about 1 to 10 hours.

Optionally, the silica-bound aggregate can be made into a very small particles which have application in fluid bed processes such as catalytic cracking. This preferably involves mixing the zeolite with a silica containing matrix solution so that an aqueous solution of zeolite and silica binder is formed which can be sprayed dried to result in small fluidizable silica-bound aggregate particles. Procedures for preparing such aggregate particles are known to persons skilled in the art. An example of such a procedure is described by Scherzer (Octane-Enhancing Zeolitic FCC Catalysts, Julius Scherzer, Marcel Dekker, Inc. New York, 1990). The fluidizable silica-bound aggregate particles, like the silica bound extrudates described above, would then undergo the final step described below to convert the silica binder to a second zeolite.

The final step in the three step catalyst preparation process is the conversion of the silica present in the silica-bound catalyst to a second zeolite which serves to bind the first zeolite crystals together. The first zeolite crystals are thus held together without the use of a significant amount of non-zeolite binder. To prepare the zeolite bound zeolite catalyst, the silica-bound aggregate can be first aged in an appropriate aqueous solution at an elevated temperature. Next, the contents of the solution and the temperature at which the aggregate is aged should be selected to convert the amorphous silica binder into the second zeolite. It is preferable that the second zeolite be of the same type as the first zeolite. The newly-formed zeolite is produced as crystals. The crystals may grow on and/or adhere to the initial zeolite crystals, and may also be produced in the form of new intergrown crystals, which are generally much smaller than the initial crystals, e.g., of sub-micron size. These newly formed crystals may grow together and interconnect.

The nature of the aluminosilicate zeolite formed in the secondary synthesis conversion of the silica to zeolite may vary as a function of the composition of the secondary synthesis solution and synthesis aging conditions. The secondary synthesis solution is preferably an aqueous ionic solution containing a source of hydroxyl ions sufficient to convert the silica to the desired zeolite.

The zeolite bound zeolite catalyst is usually in the acidic or partially neutralized acidic form. In order to obtain the acidic form, the zeolite is ion exchanged to produce the ammonium salt form. As a result of calcination, the acid form of the zeolite bound zeolite catalyst is produced.

In a more preferred embodiment, the zeolite bound zeolite catalyst is selectivated to improve its paraxylene selectivity. Processes for selectivating the catalyst are known to persons skilled in the art. For instance, selectivation may be accomplished by exposing the catalyst in a reactor bed to a thermally decomposable organic compound, e.g., toluene, at a temperature in excess of the decomposition temperature of said compound, e.g., from about 480° C. to about 650° C., more preferably 540° C. to 650° C., at a WHSV in the range of from about 0.1 to 20 lbs. of feed per pound of catalyst per hour, at a pressure in the range of from about 1 to 100 atmospheres, and in the presence of 0 to about 2 moles of hydrogen, more preferably from about 0.1 to abut 1 moles of hydrogen per mole of organic compound, and optionally in the presence of 0–10 moles of nitrogen or another inert gas per mole of organic compound. This process is conducted for a period of time until a sufficient quantity of coke has deposited on the catalyst surface, generally at least about 2% by weight and more preferably from about 8 to about 40% by weight of coke. In a preferred embodiment, such a selectivation process is conducted in the presence of hydrogen in order to prevent rampant formation of coke on the catalyst. The initial mole ratio of hydrogen gas to toluene present in the toluene feed stream can be reduced during the selectivation process after a significant amount of coke has been deposited on the catalyst surface.

Selectivation of the catalyst can also be accomplished using organosilicon compounds. The silicon compounds may comprise a polysiloxane including silicones, a siloxane, and a silane including disilanes and alkoxysilanes.

Silicone compounds which can be used in the present invention can be characterized by general formula:

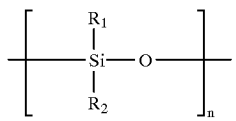

wherein $R_1$ is hydrogen, fluoride, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, and n is an integer of at least 2 and generally in the range of 2 to 1000. The molecular weight of the silicone compound employed is generally between 80 and 20,000 and preferably 150 to 10,000. Representative silicone compounds included dimethylsilicone, diethylsilicone, phenylmethylsilicone, methyl hydrogensilicone, ethylhydrogensilicone, phenylhydrogensilicone, methylethylsilicone, phenylethylsilicone, diphenylsilicone, methyltri fluoropropylsilicone, ethyltrifiluoropropylsilicone, tetrachlorophenyl methyl silicone, tetrachlorophenylethyl silicone, tetrachloro phenylhydrogen silicone, tetrachlorophenylphenyl silicone, methylvinylsilicone and ethylvinylsilicone. The silicone compound need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes or polysiloxanes include as non-limiting examples hexamethylcyclotrisiloxane, octamethylcyclotetrasiloxane, decamethyl cyclopentasiloxane, hexamethyldisiloxane, octamethytrisiloxane, decamethyltetrasiloxane, hexaethylcyclotrisiloxane, octaethylcyclo tetrasiloxane, hexaphenylcyclotrisiloxane and octaphenylcyclo tetrasiloxane.

Useful silanes, disilanes, or alkoxysilanes include organic substituted silanes having the general formula:

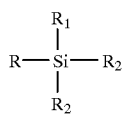

wherein R is a reactive group such as hydrogen, alkoxy, halogen, carboxy, amino, acetamide, trialkylsilyoxy $R_1$, $R_2$ and $R_3$ can be the same as R or can be an organic radical which may include alkyl of from 1 to 40 carbon atoms, alkyl or aryl carboxylic acid wherein the organic portion of the alkyl contains 1 to 30 carbon atoms and the aryl group contains 6 to 24 carbon which may be further substituted, alkylaryl and arylalkyl groups containing 7 to 30 carbon atoms. Preferably, the alkyl group for an alkyl silane is between 1 and 4 carbon atoms in chain length. Mixtures may also be used.

The silanes or disilanes include, as non-limiting examples, dimethylphenylsilane, phenytrimethylsilane, triethylsilane and hexa methyldisilane. Useful alkoxysilanes are those with at least one silicon-hydrogen bond.

The methylation process can be carried out as a batch type, semi-continuous or continuous operation utilizing a fixed or moving bed catalyst system. Multiple injection of the methylating agent may be employed.

Toluene and the methylating agent are usually premixed and fed together into the reaction vessel to maintain the desired ratio between them with no local concentration of either reactant to disrupt reaction kinetics. Individual feeds can be employed, however, if care is taken to insure good mixing of the reactant vapors in the reaction vessel. Instantaneous concentration of methylating agent can be kept low by staged additions thereof. By staged additions, toluene/ methylating agent concentrations can be maintained at optimum levels to give good toluene conversions. Hydrogen gas can be supplied to the reaction as an anticoking agent and diluent.

In carrying out the process, the catalyst and reactants can be heated to reaction temperature separately or together. Reaction temperatures are from about 300° C. to about 700° C. and preferably about 400° C. to about 700° C. The reaction is preferably carried out at a pressure from about 1 to 1000 psig, a weight hourly space velocity of between about 1 and about 2000, a molar ratio of methylating agent to toluene between about 0.05 and about 5 and a weight hourly space velocity of between about 1 and about 200 and preferably between about 5 and about 150 weight of charge per weight of catalyst per hour. The reaction product may be separated by any suitable means.

Typical methylating agents include methanol, dimethylether, methylchloride, methylbromide and dimethylsulfide. One skilled in the art will know that other methylating agents may be employed in the process of this invention based on the description provided therein. Preferred methylating agents are methanol and dimethylether. Methanol is most preferred.

The following examples illustrate the invention:

EXAMPLE 1

I. Catalyst A

Catalyst A comprised 70 wt. % H-ZSM-5 core crystals (average particle size of 3.5 microns) having a silica to alumina mole ratio of 75:1 and 30 wt. % ZSM-5 binder crystals having a silica to mole ratio of approximately 900:1. The catalyst was prepared by first mixing the ZSM-5 core crystals with amorphous silica containing a trace amount of alumina and then extruding the mixture into a silica bound extrudate. Next, the silica binder of the extrudate was converted to the second zeolite by aging the aggregate at elevated temperatures in an aqueous solution containing a template and hydroxy ions sufficient to covert the silica to the binder crystals. The resulting zeolite bound zeolite was then washed, dried, calcined, and ion exchanged into the hydrogen form.

II. Catalyst B

Catalyst B comprised 70 wt. % H-ZSM-5 (average particle size 3.5 microns) having a silica to alumina mole ratio of 75:1 and 30 wt. % amorphorous silica binder.

Toluene methylation tests were carried out using Catalyst A and Catalyst B. Prior to the start of the tests, each catalyst was crushed and sized between 30 U.S. mesh and +40 U.S. mesh sieves. Then, an amount of 1.5 grams of catalyst was mixed with 3 grams of 14/20 mesh sized quartz chips and packed into a tubular reactor. Next, a 3.8/1 molar mixture of toluene to methanol was vaporized and was fed to the reactor. The conditions of the test included a WHSV of 12, a temperature of 400° C., 450 mL/min of $N_2$, and a total pressure of 6.0 psig. The results are shown below in Table I:

TABLE I

| Catalyst | Time on Stream (hr) | Toluene Conv. (%) | Xylenes Yield % | Para-xylene Selectivity (%) | $C_1$–$C_3$ (Wt. %) |
|---|---|---|---|---|---|
| A | 1.55 | 11.7 | 73.3 | 57.6 | 1.6 |
| B | 9.45 | 19 | 70.7 | 30.9 | 0.9 |

*PX selectivity = (PX/[PX + MX + OX]) × 100

The data shows that Catalyst A had a para-xylene selectivity considerably greater than thermodynamic equilibrium and also greater than amorphous silica bound catalyst.

Catalyst A was selectivated with hexamethyldisiloxane (HMDS). The feed comprised 4.7 wt. % hexamethyldisiloxane, 1.0 wt. % n-propylmercaptan, and a molar ratio of toluene to methanol of 3.8:1. The feed was pumped to a heated line where it vaporized at 325° C. and fed to the tubular reactor. The conditions of the test included a temperature of 400° C., WHSV of 12, 450 mL/min of $N_2$, and a total pressure of 6.0 psig.

The feed used to selectivate the catalyst had a ratio of toluene to methanol and contained 4.7 wt. % hexamethyldisiloxane and 1 wt. % n-propylmercaptan. The feed was vaporized and then fed to 1.5 grams of Catalyst A which was packed with 3.0 grams of quartz chips in the tubular reactor. The conditions for the selectivation were 400° C., a WHSV of 7.9, 8 mL/min of 54% $H_2$ in $N_2$, and at total pressure of 0.3–0.5 psig. The products were analyzed by in-line gas chromatography. The results are shown in Table II.

TABLE II

| Time on Stream (hr) | Toluene Conv. % | Xylenes Yield (%) | p-xylene Sel. (%) | $C_1$–$C_3$ (Wt %) |
|---|---|---|---|---|
| 0.25 | 29.4 | 53.4 | 42.6 | 0.2 |
| 1.48 | 29.4 | 53.6 | 48.2 | 0.2 |
| 2.72 | 28.5 | 55 | 51.4 | 0.2 |
| 3.95 | 27.4 | 57.8 | 52.3 | 0.2 |
| 5.18 | 26.6 | 58 | 53.3 | 0.2 |
| 6.42 | 25.9 | 60.3 | 52.8 | 0.2 |

After selectivation, Catalyst A was tested for toluene methylation using the same procedure as Example 1 except that W-HSV was 7.9 and the total pressure was 5.3–5.6 psig. The results are shown below in Table III:

TABLE III

| Time on Stream (hr) | Toluene Conv. % | Xylenes Yield (%) | p-xylene Sel. (%) | $C_1$–$C_3$ (Wt %) |
|---|---|---|---|---|
| 0.38 | 11.3 | 91.4 | 74.1 | 1.5 |
| 1.57 | 10.7 | 91.6 | 71.7 | 1.6 |

The data shows that the activity and para-xylene selectivity of Catalyst A was enhanced by selectivation.

EXAMPLE 2

A calcined zeolite bound zeolite catalyst comprising H-ZSM-5 core crystals (silica to alumina mole ratio of about 75) and bound by ZSM-5 binder crystals (silica to alumina mole ratio of about 900) was selectivated by feeding toluene across the catalyst under the conditions set forth in Table IV below:

TABLE IV

| Selectivation Conditions | | |
|---|---|---|
| Hours | | 267 |
| Temperature (°F.) | | 1100 |
| Pressure (Psig) | | 225 |
| WHSV (#Feed/#Cat/Hr) | | 1 |
| H2:Feed Toluene Ratio (moles) | Initial | 0.21:1 |
| | Final | 0.35:1 |
| Hydrocarbon Partial Pressure | Initial | 64.6 Psia |
| | Final | 62.2 Psia |

Following selectivation, toluene was alkylated with methanol using the selectivated catalyst. The test conditions and on-oil catalyst performance are shown in Table V.

TABLE V

| Test | 1 | 2 | 3 |
|---|---|---|---|
| Average Bed Temperature (°F.) | 957 | 962 | 937 |
| WHSV (lb. feed/lb. cat/hr) | 4.4 | 4.4 | 4.4 |
| Toluene/methanol Feed Ratio (wt:wt) | 8:1 | 8:1 | 8:1 |
| Time (hrs) | 1 | 4 | 7 |
| Toluene Conversion (wt. %) | 37.2 | 29:1 | 21.4 |
| Methanol Conversion (wt. %) | 100 | 100 | >98 |
| PX Selectivity (%) | 81.1 | 81.0 | 80.1 |
| Xs:BZ (molar) | 1.1 | 1.7 | 5.2 |
| Xylenes Yields (wt. % on toluene) | 16.4 | 15.0 | 12.9 |

PX selectivity = (PX/[PX + MX + OX]) × 100

The data in Table V shows that the catalyst has high selectivity to para-xylene and xylenes:benzene ratio increased with time on-stream.

What is claimed is:

1. A process for making para-xylene by reacting toluene with a methylating agent under methylation conditions in the presence of a zeolite bound zeolite catalyst which does not contain significant amounts of non-zeolitic binder and comprises:

(a) first crystals of a first intermediate pore size zeolite; and (b) a binder comprising second crystals of a second zeolite.

2. The process recited in claim 1, wherein said second crystals are intergrown and form at least a partial coating on said first crystals.

3. The process recited in claim 2, wherein said first crystals of said first zeolite have an average particle size greater than about 0.1 micron and said second crystals of said second zeolite have an average particle size that is less than said first crystals of said first zeolite.

4. The process recited in claim 3, wherein the structure type of said first zeolite and said second zeolite are independently selected from the group consisting of AEL, MFI, MEL, MTW, MTT, FER, TON, and EUO.

5. The process recited in claim 4, wherein said first zeolite is an aluminosilicate zeolite or a gallium silicate zeolite.

6. The process recited in claim 5, wherein said catalyst is prepared by aging at elevated temperature a silica-bound aggregate containing said first crystals of said first zeolite in an aqueous ionic solution containing a source of hydroxy ions sufficient to convert the silica in the aggregate to the second zeolite.

7. The process recited in claim 5 wherein said first zeolite has a silica to alumina mole ratio of from about 10:1 to about 300:1 or a silica to gallia mole ratio from about 10:1 to about 150:1.

8. The process recited in claim 3, wherein said first crystals have an average particle size from about 1 to about 6 microns.

9. The process recited in claim 7, wherein said second zeolite has a silica to alumina mole ratio greater than about 200:1 or a silica to gallia mole ratio greater than about 100:1.

10. The process recited in claim 8, wherein said second crystals have an average particle size from about 0.1 to about 0.5 microns.

11. The process recite in claim 10, wherein said zeolite bound zeolite catalyst contains less than 5% by weight of non-zeolitic binder based on weight of said first medium pore zeolite and said second medium pore zeolite.

12. The process recited in claim 5, wherein said first zeolite has an MFI structure.

13. The process recited in claim 12, wherein said second zeolite has a MTI or MIEL structure.

14. The process recited in claim 13, wherein said methylation conditions include a temperature between about 250° C. and about 750° C., a pressure within the approximate range of 1 atmosphere to 1000 psig, a weight hourly space velocity between about 1 and about 200 and a molar ratio of methylating agent to toluene between about 0.05 to about 5.

15. The process recited in claim 14, wherein said methylating agent is methanol, methyl chloride, methyl bromide, dimethylether or dimethylsulfide.

16. The process recited in claim 14, wherein said methylating agent is methanol.

17. The process recited in claim 13, wherein said second zeolite is Silicalite or Silicalite 2.

18. The process recited in claim 17, wherein said catalyst is selectivated.

19. The process recited in claim 18, wherein said selectivation agent comprises a silicon compound.

20. The process recited in claim 19, wherein said silicon compound is hexadimethyldisiloxane.

21. The process recited in claim 19, wherein said process produces a feedstream product containing greater than equilibrium amounts of para-xylene.

22. The process recited in claim 18, wherein said catalyst contains at least 2% by weight coke.

23. The process recited in claim 22, wherein said catalyst is preselectivated by contacting the catalyst with a toluene stream at a temperature in the range of between 900° F. to 1200° F. at a pressure within the range of from 1 to 100 atmospheres and a weight hourly space velocity in the range of 0.1 to 20, and wherein said toluene stream further contains hydrogen at a $H_2$/toluene ratio of 0 to about 2.

24. The process recited in claim 23, wherein the mole ratio of hydrogen to toluene in said toluene stream is from about 0.1 to about 2.

25. A process for the selective production of para-xylene which comprises reacting toluene with methanol under methylation conditions in the presence of a catalyst which does not contain significant amounts of non-zeolitic binder and comprises first crystals of ZSM-5 and a binder comprising second crystals of a zeolite selected from the group consisting of ZSM-5, ZSM-11, Silicalite 1, and Silicalite 2.

26. The process recited in claim 25, wherein said zeolite is ZSM-5 or Silicalite 1.

* * * * *